United States Patent
Abraham et al.

(10) Patent No.: US 9,724,785 B2
(45) Date of Patent: Aug. 8, 2017

(54) RADIOGRAPHIC MARKERS FOR PARTIAL PENETRATION WELDED JOINTS

(71) Applicant: SOLAR TURBINES INCORPORATED, San Diego, CA (US)

(72) Inventors: Benjamin Richard Abraham, San Diego, CA (US); Jeffrey C. Brill, Poway, CA (US); Daniel Patrick Weller, San Diego, CA (US)

(73) Assignee: Solar Turbines Incorporated, San Diego, CA (US)

( * ) Notice: Subject to any disclaimer, the term of this patent is extended or adjusted under 35 U.S.C. 154(b) by 573 days.

(21) Appl. No.: 14/278,466

(22) Filed: May 15, 2014

(65) Prior Publication Data

US 2015/0328721 A1    Nov. 19, 2015

(51) Int. Cl.
*B23K 31/12* (2006.01)
*B23K 15/00* (2006.01)
(Continued)

(52) U.S. Cl.
CPC ........ *B23K 31/125* (2013.01); *B23K 15/0006* (2013.01); *F01D 1/20* (2013.01); *F01D 5/063* (2013.01); *B23K 11/02* (2013.01); *B23K 2201/001* (2013.01); *B23P 15/008* (2013.01); *B23P 2700/13* (2013.01); *F01D 5/06* (2013.01); *F05D 2260/80* (2013.01); *G01N 23/02* (2013.01); *Y10T 29/4932* (2015.01); *Y10T 29/49323* (2015.01)

(58) Field of Classification Search
CPC .............. B23P 2700/13; B23P 15/008; B23K 2201/001; B23K 11/02; B23K 31/125; F01D 5/063; F01D 5/06; F05D 2260/80; G01N 23/02; Y10T 29/4932; Y10T 29/49323
USPC ........ 219/101, 105; 228/104; 403/270, 271; 416/201 R
See application file for complete search history.

(56) References Cited

U.S. PATENT DOCUMENTS

| 3,974,381 A | 8/1976 | Rohrle et al. |
| 4,063,062 A * | 12/1977 | Kuhnen .................. F01D 5/063 |
| | | 219/121.14 |

(Continued)

FOREIGN PATENT DOCUMENTS

| CN | 101403712 B | 9/2011 |
| JP | 09108883 | 4/1997 |

(Continued)

*Primary Examiner* — John K Fristoe, Jr.
*Assistant Examiner* — Christopher Ballman
(74) *Attorney, Agent, or Firm* — Procopio, Hargreaves & Savitch LLP

(57) ABSTRACT

A weldment member for a gas turbine engine including a forward welding member and an aft welding member. The forward welding member has an annular shape with a forward welding face formed at one end. The forward welding face has a forward radiographic marking hole formed therein. The aft welding member has an annular shape with an aft welding face formed at one end. The aft welding face has an aft radiographic marking hole formed therein. The forward welding face is aligned with the aft welding face and the forward radiographic marking hole is angularly offset from the aft radiographic marking hole.

15 Claims, 7 Drawing Sheets

(51) Int. Cl.
*F01D 1/20* (2006.01)
*B23K 11/02* (2006.01)
*F01D 5/06* (2006.01)
*B23K 101/00* (2006.01)
*B23P 15/00* (2006.01)
*G01N 23/02* (2006.01)

(56) References Cited

U.S. PATENT DOCUMENTS

| | | | | |
|---|---|---|---|---|
| 4,634,168 | A * | 1/1987 | Fuchs | B62D 33/00 |
| | | | | 280/785 |
| 4,694,479 | A | 9/1987 | Bacskai et al. | |
| 5,304,774 | A | 4/1994 | Durheim | |
| 6,341,419 | B1 * | 1/2002 | Forrester | F01D 5/027 |
| | | | | 29/889.2 |
| 8,641,845 | B2 | 2/2014 | Bruck | |
| 9,334,739 | B2 * | 5/2016 | Kepler | F01D 5/06 |
| 2002/0172587 | A1 | 11/2002 | Keller et al. | |
| 2007/0036646 | A1 * | 2/2007 | Nguyen | F04D 29/4206 |
| | | | | 415/208.3 |
| 2008/0141531 | A1 * | 6/2008 | Paulino | B23K 15/0006 |
| | | | | 29/889.22 |
| 2009/0293253 | A1 * | 12/2009 | Walker | B23P 6/005 |
| | | | | 29/402.13 |
| 2014/0064946 | A1 * | 3/2014 | Nielsen | F01D 5/06 |
| | | | | 415/199.5 |

FOREIGN PATENT DOCUMENTS

| | | |
|---|---|---|
| JP | 2001047232 | 2/2001 |
| JP | 2013108450 | 6/2013 |

* cited by examiner

RADIOGRAPHIC MARKERS FOR PARTIAL PENETRATION WELDED JOINTS

TECHNICAL FIELD

The present disclosure generally pertains to gas turbine engines, and is more particularly directed toward gas turbine engine compressor rotor assembly weldment member with radiographic markers in partial penetration welded joints.

BACKGROUND

Gas turbine engines include compressors, and turbine sections formed by welding together disks. In particular, groups of metallic disks are welded together to form weldment members to which turbine blades can be attached. In order to maintain quality control, the welds between adjacent metallic disks may be inspected using radiographic imaging processes to determine weld penetration depth.

U.S. Pat. No. 3,974,381, to Rohrle et al., discloses a welding method and apparatus for detecting the penetration depth of an electron beam weld, in which X-rays which occur are guided through several plates of an absorption device to a ray receiver. The plates comprise a plurality of bores of equal diameter, which are arranged in their position to one another in such a way that the center lines of corresponding bores on the same level are in exact alignment. The ray receiver, absorption device and work piece are aligned in parallel with one another and are coordinated to one another in height.

The present disclosure is directed toward overcoming one or more of the problems discovered by the inventors.

SUMMARY OF THE DISCLOSURE

A weldment member for a gas turbine engine is disclosed. The weldment member includes a forward welding member and an aft welding member. The forward welding member has an annular shape with a forward welding face formed at one end. The forward welding face has at least one forward radiographic marking hole formed therein. The aft welding member has an annular shape with an aft welding face formed at one end. The aft welding face has at least one aft radiographic marking hole formed therein. The forward welding face is aligned with the aft welding face and the at least one forward radiographic marking hole is angularly offset from the at least one aft radiographic marking hole.

A gas turbine engine compressor rotor assembly is also disclosed. The gas turbine engine compressor rotor assembly includes a weldment member and a plurality of compressor rotor blades. The weldment member has a plurality of compressor disks. Each of the plurality of compressor disks includes a forward welding member and an aft welding member. The forward welding member has an annular shape with a forward welding face formed at one end. The forward welding face has at least one forward radiographic marking hole formed therein. The aft welding member has an annular shape with an aft welding face formed at one end. The aft welding face has at least one aft radiographic marking hole formed therein. The forward welding face is aligned with the aft welding face and the at least one forward radiographic marking hole is angularly offset from the at least one aft radiographic marking hole. Each of the plurality of compressor disks also includes a plurality of rotor blade slots. The plurality of compressor rotor blades are each located in one of the rotor blade slots.

A method of determining weld depth penetration in a weldment member of a gas turbine engine is also disclosed. The method includes forming at least one forward radiographic marking hole in a forward welding face of a forward welding member. The method also includes forming at least one aft radiographic marking hole in an aft welding face of an aft welding member. The method also includes aligning the forward welding face of the forward welding member with the aft welding face of the aft welding member. The method further includes welding the forward welding face of the forward welding member to the aft welding face of the aft welding member using a penetration welding process. The method additionally includes radiographically imaging a portion of the weldment member to determine if the at least one forward radiographic marking hole and the at least one aft radiographic marking holes have been obscured with welding material.

DETAILED DESCRIPTION

The systems and methods disclosed herein include a gas turbine engine compressor rotor assembly with marking holes defining a weld line during radiographic inspection of the weld. In embodiments, the compressor rotor assembly includes weldments having forward and aft welding members with the marking holes formed in the welding faces thereof. The marking holes of the forward welding member may be offset from marking holes of the aft welding member during welding. After welding the one or more of the marking holes may be partially or completed filled with welding material.

Figure 1:
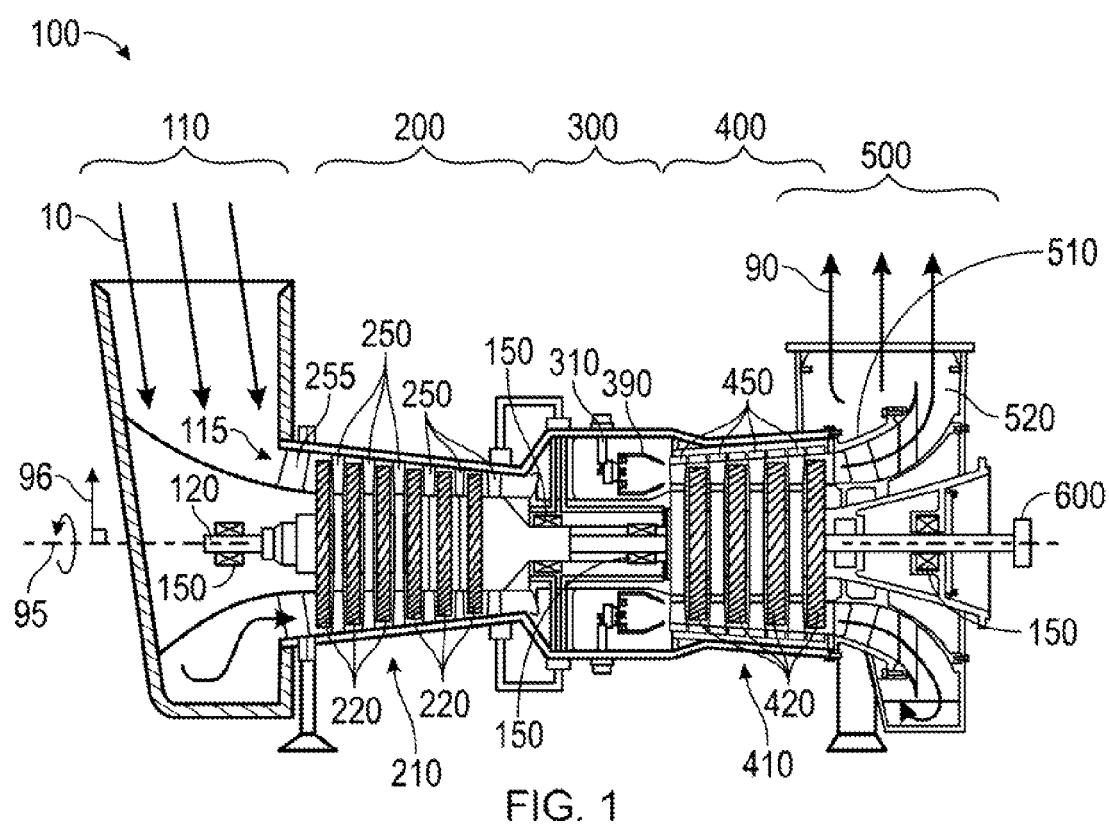
FIG. 1 is a schematic illustration of an exemplary gas turbine engine.

FIG. 1 is a schematic illustration of an exemplary gas turbine engine. Some of the surfaces and structures have been left out or exaggerated (here and in other figures) for clarity and ease of explanation. Also, the disclosure may reference a forward and an aft direction. Generally, all references to "forward" and "aft" are associated with the flow direction of primary air (air which is used in the Brayton cycle, the thermodynamic basis for gas turbine operation), unless specified otherwise. For example, forward is "upstream" relative to primary air flow, and aft is "downstream" relative to primary air flow.

In addition, the disclosure may generally reference a center axis 95 of rotation of the gas turbine engine, which may be generally defined by the longitudinal axis of its shaft 120 (supported by a plurality of bearing assemblies 150). The center axis 95 may be common to or shared with various other engine concentric components. All references to radial, axial, and circumferential directions and measures refer to center axis 95, unless specified otherwise, and terms such as "inner" and "outer" generally indicate a lesser or greater radial distance from, wherein a radial 96 may be in any direction perpendicular and radiating outward from center axis 95.

A gas turbine engine 100 includes an inlet 110, a shaft 120, a gas producer or "compressor" 200, a combustor 300, a turbine 400, an exhaust 500, and a power output coupling 600. The gas turbine engine 100 may have a single shaft or a dual shaft configuration.

The compressor 200 includes a compressor rotor assembly 210, compressor stationary vanes ("stators") 250, and inlet guide vanes 255. The compressor rotor assembly 210 mechanically couples to shaft 120. As illustrated, the compressor rotor assembly 210 is an axial flow rotor assembly. The compressor rotor assembly 210 may include one or more weldments 211 coupled by interference fits and dowel pins to one another, which may be coupled to the forward hub 213 (shown in FIG. 2) which also may be coupled by interference fits or curvics. The weldment 211 each include one or more compressor disk assemblies 220. Each compressor disk assembly 220 includes a compressor disk 221 (shown in FIGS. 2 and 3) that is circumferentially populated with compressor rotor blades 229.

Stators 250 axially follow each of the compressor disk assemblies 220. Each compressor disk assembly 220 paired with the adjacent stators 250 that follow the compressor disk assembly 220 is considered a compressor stage. Compressor 200 includes multiple compressor stages. Inlet guide vanes 255 axially precede the first compressor stage.

The combustor 300 includes one or more injectors 310 and includes one or more combustion chambers 390.

The turbine 400 includes a turbine rotor assembly 410 and turbine nozzles 450. The turbine rotor assembly 410 mechanically couples to the shaft 120. As illustrated, the turbine rotor assembly 410 is an axial flow rotor assembly. The turbine rotor assembly 410 includes one or more turbine disk assemblies 420. Each turbine disk assembly 420 includes a turbine disk that is circumferentially populated with turbine blades. Turbine nozzles 450 axially precede each of the turbine disk assemblies 420. Each turbine disk assembly 420 paired with the adjacent turbine nozzles 450 that precede the turbine disk assembly 420 is considered a turbine stage. Turbine 400 includes multiple turbine stages.

The exhaust 500 includes an exhaust diffuser 510 and an exhaust collector 520.

Figure 2:
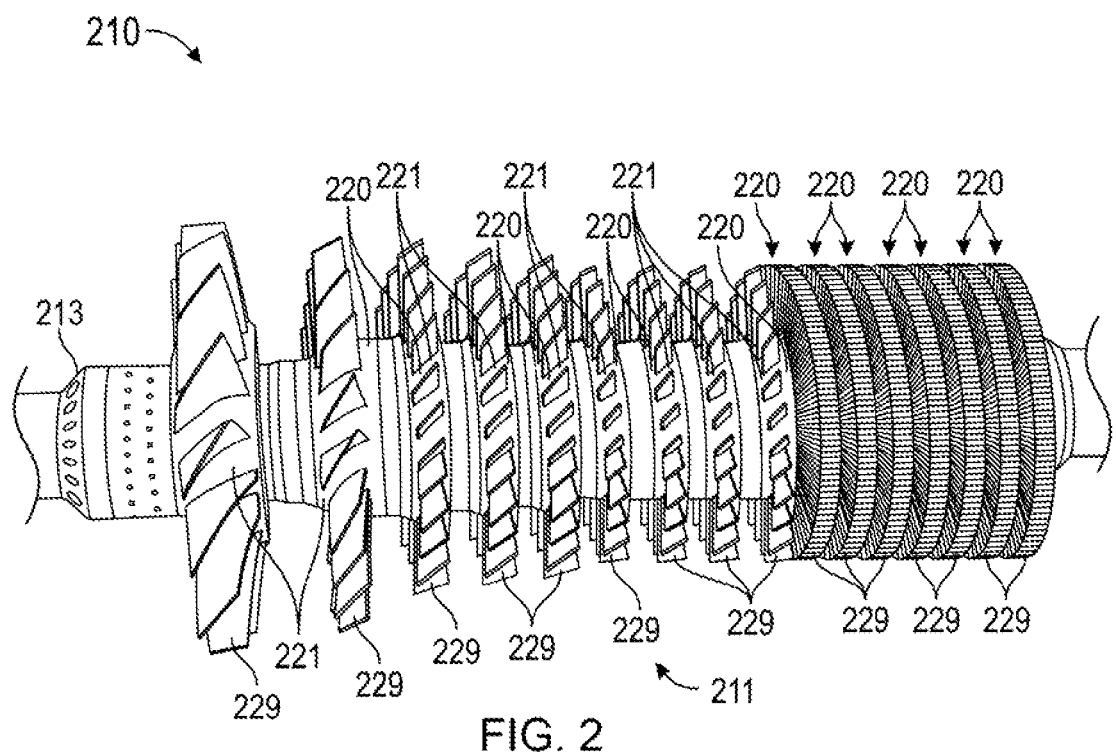
FIG. 2 is a perspective view of the compressor rotor assembly of the gas turbine engine of FIG. 1.

FIG. 2 is a perspective view of the compressor rotor assembly 210 of FIG. 1. The compressor rotor assembly 210 may include compressor rotor blades 229. The compressor rotor blades 229 may be axially installed compressor rotor blades ("axial blades"), circumferentially installed compressor rotor blades ("circumferential blades"), or a combination of axial blades and circumferential blades. The Compressor rotor blade sizes may be determined by the sizes of the compressor disks 221.

Figure 3:
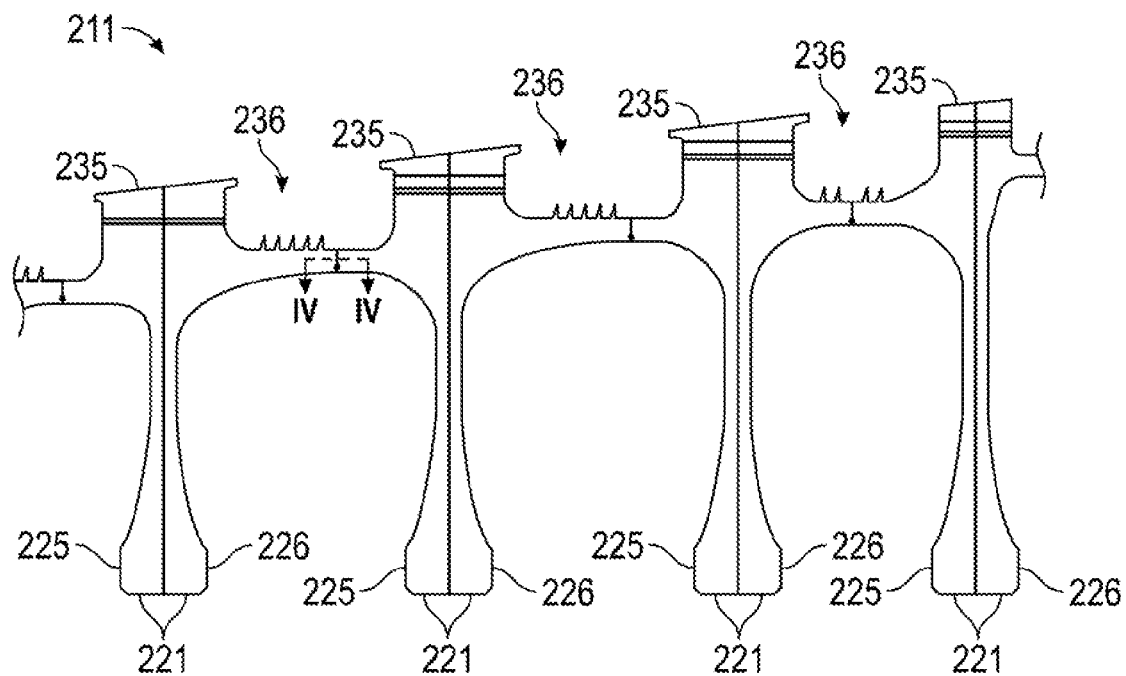
FIG. 3 is a cross-sectional view of a portion of the weldment of the compressor rotor assembly of FIG. 2.

FIG. 3 is a cross-sectional view of a portion of the weldment 211 of the compressor rotor assembly 210 of FIG. 2. The weldment 211 includes multiple compressor disks 221. Each of the compressor disks 221 may include a forward welding member 226 and an aft welding member 225. The forward welding member 226 may have an annular shape and may extend forward from each of the compressor disk 221. The aft welding member 225 may have an annular shape and may extend aft from the compressor disk 221. The aft welding member 225 of a compressor disk 221 of a first stage may be welded to the forward welding member 226 of a compressor disk 221 of a subsequent stage. Each subsequent compressor disk 221 may be welded to the previous compressor disk 221 in a similar manner.

Each compressor disk 221 of the weldment 211 may include a peripheral flange 235 forming one or more a rotor blade slots 236. In some embodiments, the each rotor blade slot 236 may be either an axial slot or a circumferential slot. One or more compressor rotor blades 229 may be inserted into each of the rotor blade slots 236. If the compressor disk 221 has one or more axial slots, one axial blade may be inserted into each axial slot. If the compressor disk 221 has a circumferential slot, multiple circumferential blades may be inserted into the circumferential slot. In the embodiment shown in FIG. 3, five compressor disks 221 having rotor blade slots 236 that are axial slots. In other embodiments, the rotor blade slots 236 may be circumferential slots or a combination of axial and circumferential slots.

Figure 4:
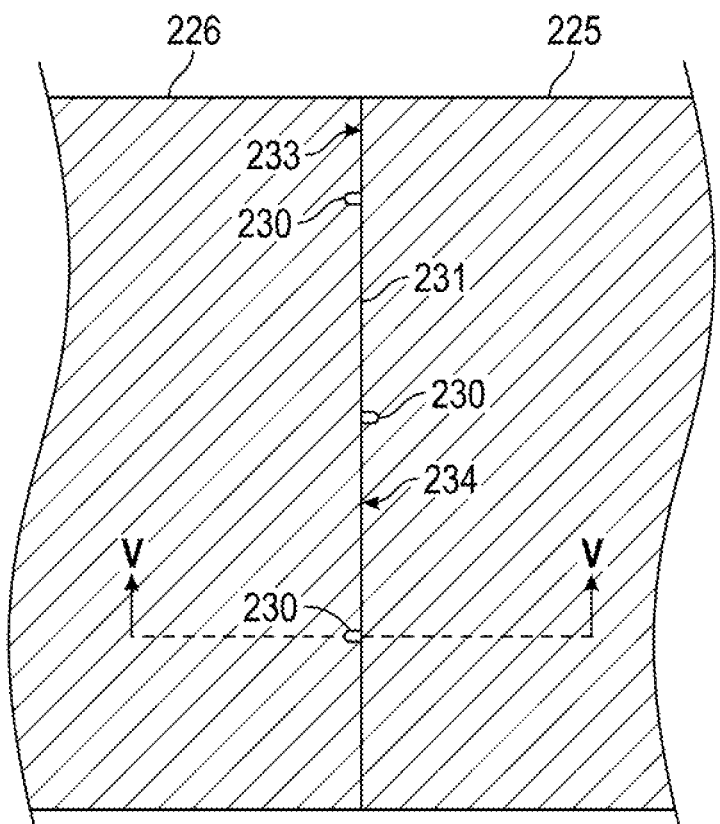
FIG. 4 is a cross-sectional view of an un-welded joint between a forward welding member and an adjacent aft welding member of the portion of the weldment of FIG. 3 taken along line VI-VI.

FIG. 4 is a cross-sectional view of an un-welded joint 231 between a forward welding member 226 and an adjacent aft welding member 225 of the portion of the weldment 211 of FIG. 3. The cross-section is taken along line VI-VI of FIG. 3. The relative size and/or distance between components may be exaggerated to aid clarity.

As illustrated, the forward welding member 226 has a generally annular shape with a forward welding face 234 formed at one end. Similarly, the aft welding member 225 has a generally annular shape with an aft welding face 233 formed at one end. The forward welding face 234 of the forward welding member 226 contacts the aft welding face 233 of the aft welding member 225 at the joint 231 between the forward welding member 226 and the aft welding member 225.

The forward welding member 226 is illustrated having a plurality of radiographic marking holes 230 formed in the forward welding face 234. However, other embodiments may have only a single radiographic marking hole 230 formed in the forward welding face 234. Radiographic marking holes 230 formed in the forward welding face 234 may be referred to as forward radiographic marking holes. In some embodiments, the diameter of these marking holes 230 may be 40 thousands of an inch. However, embodiments of the marking hole may have larger or smaller diameters. Additionally, in some embodiments, the depth of the marking hole may be in a range of 50-70 thousandths of an inch. However, other embodiments may have a larger or a smaller hole depth.

The aft welding member 225 is also illustrated having a radiographic marking hole 230 formed in the aft welding face 233. However, other embodiments may have a plurality of radiographic marking holes 230 formed in the aft welding face 233. Radiographic marking holes 230 formed in the aft welding face 233 may be referred to as aft radiographic marking holes. Again, in some embodiments, the diameter of these marking holes 230 may be 40 thousands of an inch. However, embodiments of the marking hole may have larger or smaller diameters. Further, in some embodiments, the depth of the marking hole 230 may be in a range of 50-70 thousandths of an inch. However, other embodiments may have a larger or a smaller hole depth.

FIG. 4 illustrates that the forward welding face 234 of the forward welding member 226 is positioned against the aft welding face 233 of the aft welding member 225 with the radiographic marking holes 230 of the forward welding member 226 being angularly offset from the radiographic marking holes 230 of the aft welding member 225 with respect to the central axis 95 (shown in FIG. 1). In some embodiments, the angular offset may be a 45° angle. In other embodiments, the angular offset may be a larger or smaller angle.

Figure 5:
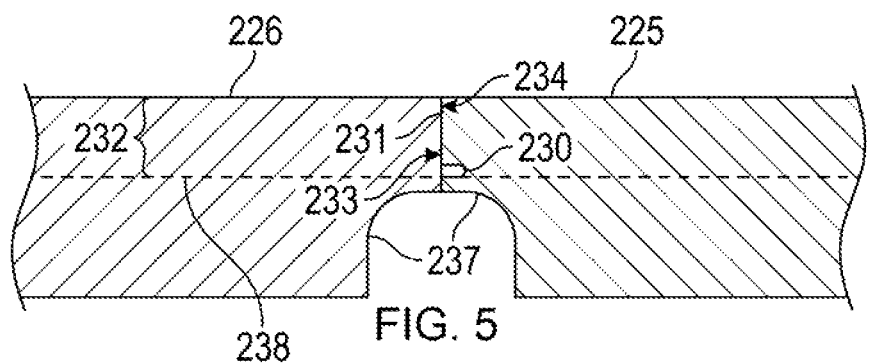
FIG. 5 is another cross-sectional view of the un-welded joint between the forward welding member and the adjacent aft welding member of the portion of weldment of FIG. 4 taken along line V-V.

FIG. 5 is another cross-sectional view of the un-welded joint 231 between the forward welding member 226 and the adjacent aft welding member 225 of the portion of weldment 211 of FIG. 4. The cross-section is taken along line V-V through one of the radiographic marking holes 230 of the forward welding member 226 of FIG. 4. The relative size and/or distance between components may be exaggerated to aid clarity.

In FIG. 5, only one radiographic marking hole 230 is visible due to the section cut illustrated and other radiographic marking holes 230 have been omitted for clarity. The radiographic marking hole 230 is located a radial distance 232 below the outer edge or circumference (upper side as illustrated in FIG. 5) of the aft welding member 225. The radial distance 232 may be measured between the outer edge or circumference of the aft welding member 225 and radially inner edge of the radiographic marking hole 230 (lower side of radiographic marking hole 230 as illustrated by reference line 238 in FIG. 5) of the radiographic marking hole. In some embodiments, the radial distance 232 may correspond to a weld penetration depth used during welding of the welding members as discussed below.

FIG. 5 also illustrates that a chamfered notch 237 may be provided adjacent to the forward welding face 234 of the forward welding member 226. Similarly, a chamfered notch 237 may also be provided adjacent to the aft welding face 233 of the aft welding member 225.

Figure 6:
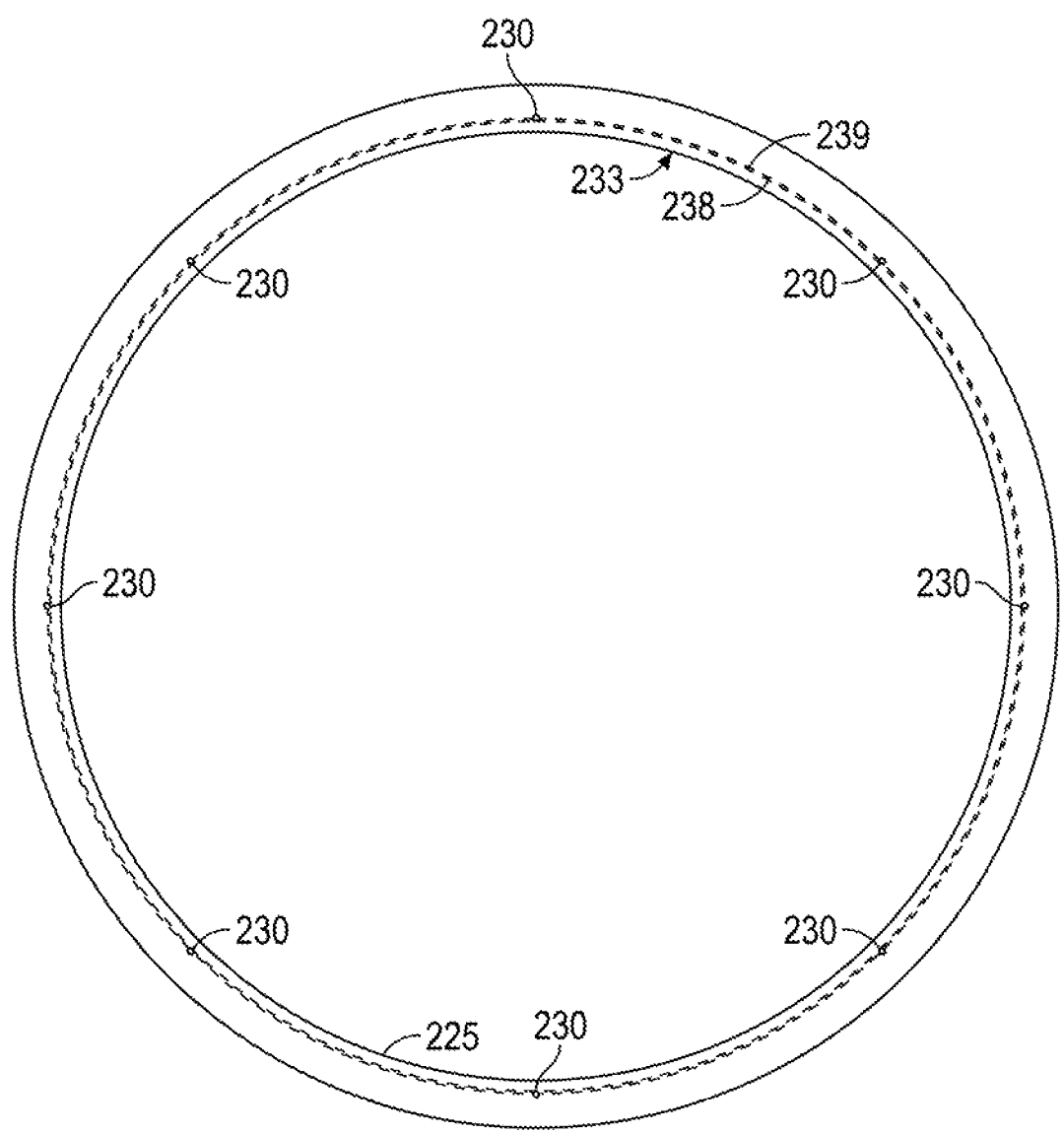
FIG. 6 is an end view of a welding face of one of the welding members of the portion of the weldment of FIG. 3.
Figure 7:
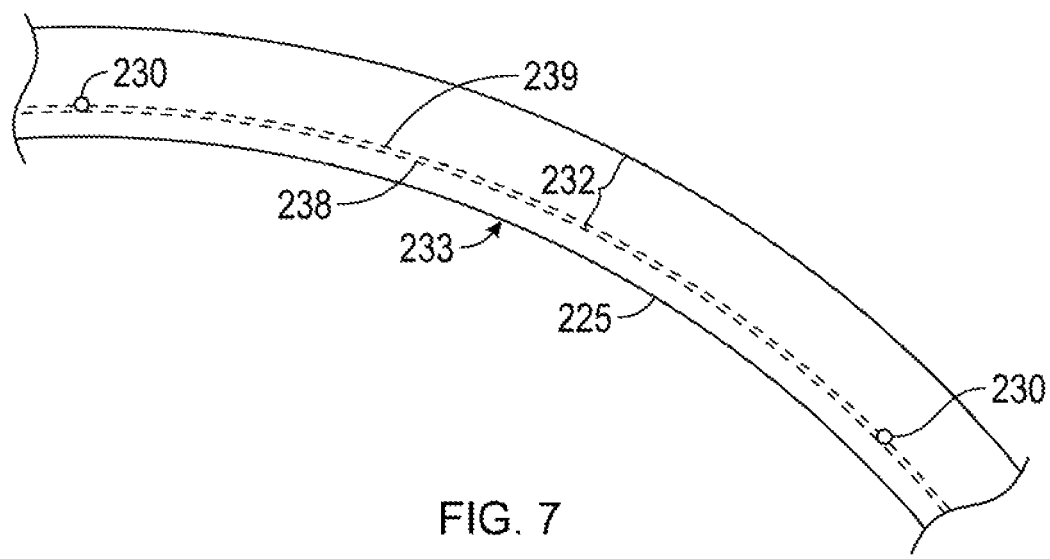
FIG. 7 is an enlarged view of a portion of the welding face of the welding member of FIG. 6.

FIG. 6 is an end view of the aft welding face 233 of the aft welding member 225 of the portion of the weldment of FIG. 3. FIG. 7 is an enlarged view of a portion of the aft welding face 233 of the aft welding member 225 of FIG. 6. The forward welding face 234 of the forward welding member 226 is structurally similarly to the aft welding face 233 illustrated in FIGS. 6 and 7 and redundant illustration of the forward welding face 234 of the forward welding member 226 is therefore omitted.

In the embodiment of FIG. 6, eight radiographic marking holes 230 are provided in the aft welding face 233 of the aft welding member 225. However, in other embodiments, more or less than eight radiographic marking holes 230 may be provided. For example, four radiographic marking holes may be provided in the aft welding face 233. Additionally, a similar number of radiographic marking holes 230 may also be provided in the forward welding face 234.

As illustrated, the radiographic marking holes 230 are positioned at equally spaced angular positions around a circumference of the aft welding face 233. The geometric center of each of the radiographic marking holes 230 is located at a common radial position as illustrated by reference line 239. The radiographic marking holes 230 are illustrated as having a circular cross-section. However, the radiographic marking holes 230 are not limited to this configuration and may have other shapes such as an oval, a square, or any other shape that may be apparent to a person of ordinary skill in the art.

Further as illustrated in FIG. 7, each radiographic marking hole 230 is located a radial distance 232 below the radially outer edge or circumference of the aft welding member 225. The radial distance 232 may be measured between the outer edge or circumference of the aft welding member 225 and radially inner edge of the radiographic marking hole 230 (lower side of radiographic marking hole 230 as illustrated by the reference line 238 in FIG. 5) of the radiographic marking hole. As mentioned above, the radial distance 232 may correspond to a weld penetration depth used during welding of the welding members as discussed below.

Figure 8:
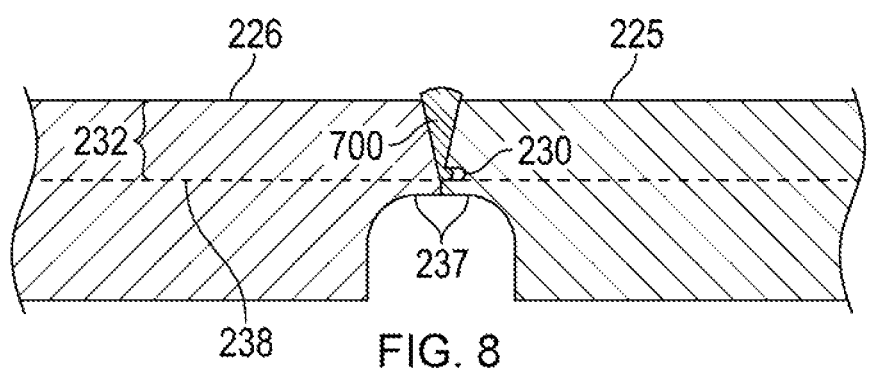
FIG. 8 is another cross-sectional view of a welded joint between the forward welding member and the adjacent aft welding member adjacent welding members of the portion of weldment of FIG. 4 taken along line V-V.

FIG. 8 is a cross-sectional view of the joint 231 between the forward welding member 226 and the adjacent aft welding member 225 of the portion of weldment 211 shown in FIG. 4 after the joint has been welded. FIG. 8 shows the same features illustrated in FIG. 5 discussed above and uses the same reference numerals for the same components. As with FIG. 5, the cross-section is taken along line V-V of FIG. 3.

A weld 700 has been formed between the forward welding member 226 and the aft welding member 225. In some embodiments, the weld 700 includes welding material that has flown into one of more of the radiographic marking holes 230. In some embodiments, all of the radiographic marking holes 230 may be completely filled by welding material from the weld 700. However, in other embodiments, only a few or even only one of the radiographic marking holes 230 may be completely filled and the remaining radiographic marking holes 230 may be only partially filled. Further, in some embodiments, one or more radiographic marking holes 230 may remain completely unfilled by welding material from the weld 700.

INDUSTRIAL APPLICABILITY

Gas turbine engines may be suited for any number of industrial applications such as various aspects of the oil and gas industry (including transmission, gathering, storage, withdrawal, and lifting of oil and natural gas), the power generation industry, cogeneration, aerospace, and other transportation industries.

Referring to FIG. 1, a gas (typically air 10) enters the inlet 110 as a "working fluid", and is compressed by the compressor 200. In the compressor 200, the working fluid is compressed in an annular flow path 115 by the series of compressor disk assemblies 220. In particular, the air 10 is compressed in numbered "stages", the stages being associated with each compressor disk assembly 220. For example, "4th stage air" may be associated with the 4th compressor disk assembly 220 in the downstream or "aft" direction, going from the inlet 110 towards the exhaust 500). Likewise, each turbine disk assembly 420 may be associated with a numbered stage.

Once compressed air 10 leaves the compressor 200, it enters the combustor 300, where it is diffused and fuel is added. Air 10 and fuel are injected into the combustion chamber 390 via injector 310 and combusted. Energy is extracted from the combustion reaction via the turbine 400 by each stage of the series of turbine disk assemblies 420. Exhaust gas 90 may then be diffused in exhaust diffuser 510, collected and redirected. Exhaust gas 90 exits the system via an exhaust collector 520 and may be further processed (e.g., to reduce harmful emissions, and/or to recover heat from the exhaust gas 90).

Gas turbine engines and other rotary machines include a number of rotating elements rotating at high speeds and experience high thermal and mechanical stresses. Therefore, the welds between components, such as the forward welding member 226 and aft welding member 225 of the compressor disks 221 of the weldment, are usually inspected during assembly and at regular maintenance schedules to detect flaws that may result in failure of the components during operation.

As illustrated in FIGS. 3, 4, 5, 6, 7, and 8, the weldment member 211 of the compressor rotor assembly 210 is formed by a plurality of compressor disks 221. Each compressor disk 221 is formed from a forward welding member 226 having a forward welding face 234 and an aft welding member 225 having an aft welding face 233. During assembly of each compressor disk 221, the forward welding face 234 is welded to the aft welding face 233. Typical welding processes include, but are not limited to, electron-beam welding process, laser-beam welding process, or any other narrow beam, high energy welding process that may be apparent to a person of ordinary skill in the art.

Embodiments of the present application include one or more radiographic marking holes 230 in both the forward welding face 234 and the aft welding face 233 that can be used to determine weld depth penetration during weld inspection.

Figure 9:
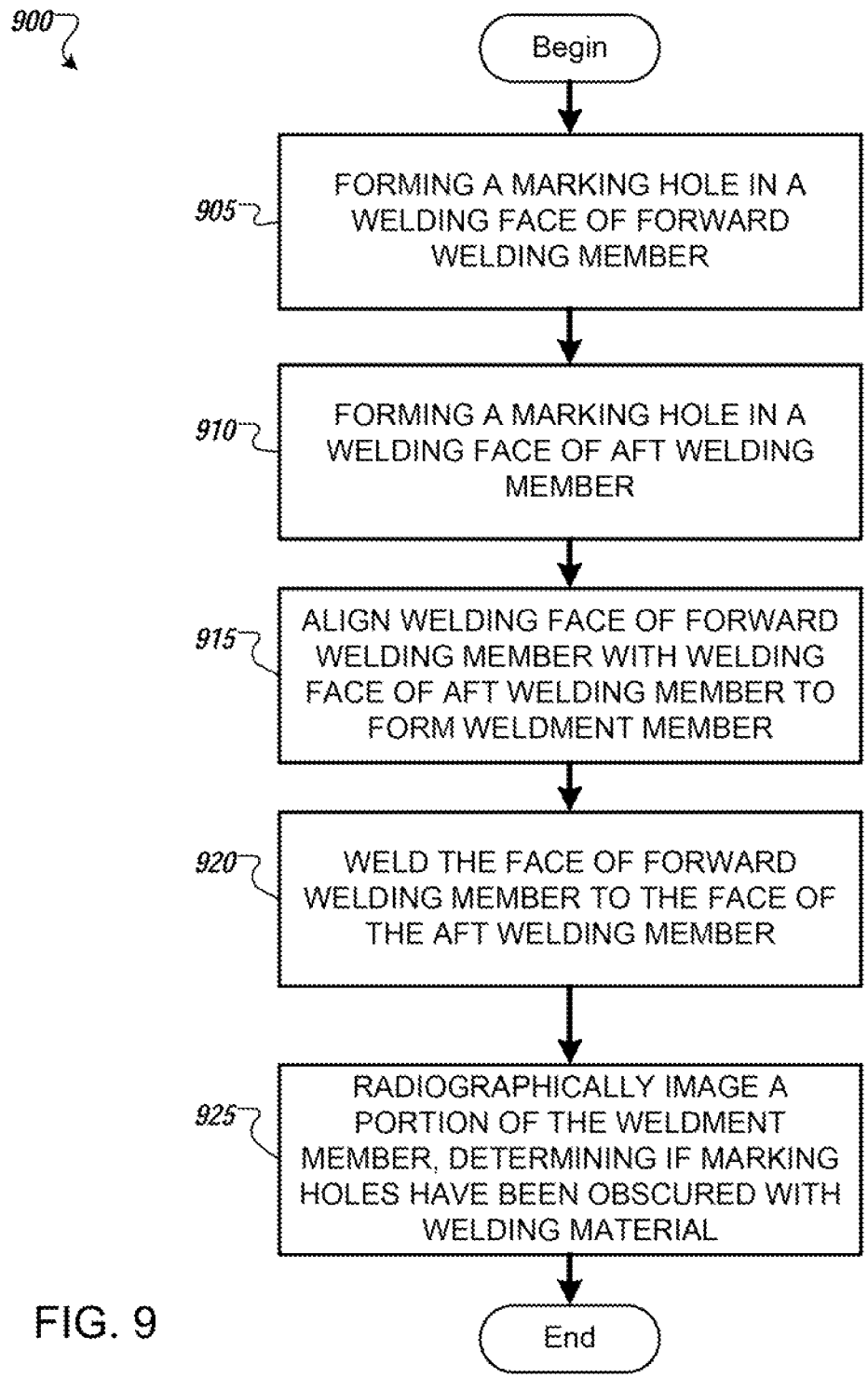
FIG. 9 is a flowchart of a method for determining weld depth penetration in a weldment member for a gas turbine engine.

FIG. 9 is a flowchart of a method 900 for inspecting the weld 700 and determining weld depth penetration in a weldment member 211 for a gas turbine engine 100. In step 905, at least one radiographic marking hole 230 is formed in the forward welding face 234 of the forward welding member 226. The radiographic marking hole 230 may be placed a radial distance 232 from the radially outer edge or circumference of the forward welding member 226. The radial distance 232 may be measured between the outer edge or circumference of the forward welding member 226 and radially inner edge of the radiographic marking hole 230 (lower side of radiographic marking hole 230 as illustrated by the reference line 238 in FIG. 5).

The radiographic marking hole 230 may be formed by drilling, milling, or other machining process that may be apparent to a person of ordinary skill in the art. In some embodiments, the radiographic marking hole 230 may be formed as a circular hole having a diameter of 40 thousandths of an inch and hole depth in a range of 50-70 thousandths of an inch. In other embodiments, the radiographic marking hole 230 may have a different shape or may have larger or smaller dimensions as discussed above. However, if the size or shape of the radiographic marking hole becomes too large, the radiographic marking hole 230 may create a failure point in the forward welding member 226 that could cause potential failure during operation.

Similarly, in step 910, at least one radiographic marking hole 230 is formed in the aft welding face 233 of the aft welding member 225. The radiographic marking hole 230 may be placed a radial distance 232 from the radially outer edge or circumference of the aft welding member 225. The radial distance 232 may be measured between the outer edge or circumference of the aft welding member 225 and radially inner edge of the radiographic marking hole 230 (lower side of radiographic marking hole 230 as illustrated by the reference line 238 in FIG. 5).

The radiographic marking hole 230 may be formed by drilling, milling, or other machining process that may be apparent to a person of ordinary skill in the art. In some embodiments, the radiographic marking hole 230 may be formed as a circular hole having a diameter of 40 thousandths of an inch and hole depth in a range of 50-70 thousandths of an inch. In other embodiments, the radiographic marking hole 230 may have a different shape or may have larger or smaller dimensions as discussed above. However, if the size or shape of the radiographic marking hole 230 becomes too large, the radiographic marking hole 230 may create a failure point in the aft welding member 225 that could cause potential failure during operation.

In step 915, the forward welding face 234 of the forward welding member 226 is aligned to the aft welding face 233 of the aft welding member 225. More specifically, the forward welding face 234 is aligned with the aft welding face 233 so that the one or more radiographic marking holes 230 formed in the forward welding face 234 is angularly offset from the one or more radiographic marking holes 230 formed in the aft welding face 233. In some embodiments, the angular offset may be 45°. In some embodiments, the angular offset may be more or less than 45°. In some embodiments, the forward welding face 234 may be manually aligned with the aft welding face 233 by a human. In other embodiments, the forward welding face 234 may be automatically aligned with the aft welding face 233 by an automated assembly machine using machine vision.

After the forward welding face 234 is aligned with the aft welding face 233 with the respective radiographic marking holes 230 angularly offset from each other in step 915, the forward welding member 226 is welded to the aft welding member 225 along the joint 231 (illustrated in FIGS. 4 and 5) in step 920. The welding process may be a penetration welding process and may include electron-beam welding, laser-beam welding, or any other narrow beam, high energy welding process that may be apparent to a person of ordinary skill in the art. During the welding process, the energy intensity may be set to a level to produce a specific amount of penetration by the high-energy beam as is known in the art. For example, the energy intensity may be set to produce a minimum penetration of 75% of the thickness of the welding member. In some embodiments, the maximum penetration may be up to 95%, and in some cases the maximum weld penetration may be well below 95%.

In some embodiments, the minimum penetration set to be produced during the welding may correspond to the radial distance 232 between the outer edge or circumference of the respective welding member (i.e. forward welding member 226 and aft welding member 225) and the radially inner edge of the radiographic marking hole 230 (illustrated by the reference line 238 in FIG. 5). For example, the radial distance 232 between the outer edge or circumference of the welding member and the radially inner edge of the radiographic marking hole 230 may correspond to 75% of the thickness of the welding member if the energy intensity is to be set to produce a minimum penetration of 75% of the thickness of the welding member.

In step 925, after the forward welding member 226 has been welded to the aft welding member 225, a portion of the weldment 211 around the weld 700 may be radiographically imaged. Specifically, the weld 700 may be radiographically imaged by passing non-visible electromagnetic radiation through the weld 700 from a generator on one side of the weld 700 to a detector on an opposite side of the weld 700. For example, the radiation generator may be placed on a radially outer side of the weld 700 and the radiation detector may be placed on a radially inner side of the weld 700. In some embodiments, the radiographic imaging may produce still images used to evaluate sections or portions of the weld 700. In other embodiments, the radiographic imaging may produce video that may be used to evaluate the entire weld 700 as the weldment 211 is rotated relative to the radiation generator and radiation detector.

The type of non-visible electromagnetic radiation passed through the weld is not particularly limited and may include X-ray radiation, Gamma-Ray radiation, and any other form of radiation that may be apparent to a person of ordinary skill in the art.

Using the radiographic images produced during the radiographic imaging, the penetration depth and weld alignment can be visually inspected. Specifically, the radiographic marking holes 230 on the forward welding face 234 side of the weld 700 and the aft welding face 233 side of the weld 700 are generally visible on the radiographic image if no welding material from the weld 700 has flowed into the radiographic marking holes. As the radiographic marking holes 230 are filled with welding material from the weld 700, the visibility of the radiographic marking hole 230 on the radiographic image will diminish and may be completely lost if the radiographic marking hole 230 is completely filled.

The weld penetration depth and weld alignment may be determined to be within acceptable tolerances and deemed to be a good weld if all or a majority of the radiographic marking holes 230 on the forward welding face 234 side of the weld 700 and the aft welding face 233 have been completely or substantially obscured by welding material flowing into the radiographic marking holes 230 from the weld 700. Conversely, if all or most of the radiographic marking holes 230 are completely visible on the radiographic image the weld penetration depth and/or weld alignment may be determined to unacceptable and the weld 700 rejected. The specific number of visible radiographic marking holes or the degree of visibility that determines whether a weld is acceptable or rejected may vary depending on the needed design parameters of the parts being welded as may be apparent to a person of ordinary skill in the art. For example, some weld design parameters may require a 100% fill rate of the radiographic marking holes to be deemed an acceptable weld in some embodiments. In other embodiments, a 95% fill rate, a 90% fill rate, an 85% fill rate, etc. may be acceptable.

By providing a process to visually inspect the welds and quantify levels of weld penetration, improved weld quality, and reduced weld failure may be produced. As weld quality is improved, and weld failure rates are reduced, product life may be extended resulting in repair/replacement cost savings and reduced equipment down time.

The preceding detailed description is merely exemplary in nature and is not intended to limit the invention or the application and uses of the invention. The described embodiments are not limited to use in conjunction with a particular type of gas turbine engine. Hence, although the present disclosure, for convenience of explanation, depicts and describes a particular forward welding member, a particular aft welding member, and associated processes, it will be appreciated that other forward welding members, aft welding members, and processes in accordance with this disclosure can be implemented in various other compressor rotor assemblies, configurations, and types of machines. Furthermore, there is no intention to be bound by any theory presented in the preceding background or detailed description. It is also understood that the illustrations may include exaggerated dimensions to better illustrate the referenced items shown, and are not consider limiting unless expressly stated as such.

Additionally, the above discussed embodiments relate to welding of compressor rotor disks of a weldment of a compressor rotor assembly of a gas turbine engine. However, embodiments of the present application are not limited to these components and may also relate to other welded components of the gas turbine engine.

What is claimed is:

1. A weldment member foe a gas turbine engine comprising:
   a gas turbine having
      a plurality of turbine disk assemblies, each disk assembly comprising:
      a forward welding member having an annular shape with a forward welding face formed at one end of the annular shape, the forward welding face having at least one forward radiographic marking hole formed therein; and
      an aft welding member having an annular shape with an aft welding face formed at one end of the annular shape, the aft welding face having at least one aft radiographic marking hole formed therein,
      wherein the forward welding face of the forward welding member is aligned with the aft welding face pf the aft welding member and the at least one forward radiographic marking hole is offset from the at least one aft radiographic marking hole angularly.

2. The weldment member of claim 1, further comprising a plurality of forward radiographic marking holes equally spaced around a circumference of the forward welding member;
   a plurality of aft radiographic marking holes equally spaced around a circumference of the aft welding member; and
   wherein each of the forward radiographic marking holes is offset angularly from each of the aft radiographic marking holes.

3. The weldment member of claim 1, wherein the at least one forward radiographic marking hole has a diameter less than or equal to 40 thousandths of an inch; and
   wherein the at least one aft radiographic marking hole has a diameter less than or equal to 40 thousandths of an inch.

4. The weldment member of claim 1, wherein the at least one forward radiographic marking hole has a hole depth greater than or equal to 50 thousandths of an inch and less than or equal to 70 thousandths of an inch; and
   wherein the at least one aft radiographic marking hole has a hole depth greater than or equal to 50 thousandths of an inch and less than or equal to 70 thousandths of an inch.

5. The weldment member of claim 1, wherein a radially inner edge of the at least one forward radiographic marking hole is disposed a distance from an outer edge of the forward welding member, the distance being equal to a weld penetration depth of the weldment member; and
   wherein a radially inner edge of the at least one aft radiographic marking hole is disposed a distance from an outer edge of the aft welding member, the distance being equal to a weld penetration depth of the weldment member.

6. The weldment member of claim 5, wherein the weld penetration depth of the weldment member is 75% of a thickness of the weldment member.

7. The weldment member of claim 1, wherein the at least one forward radiographic marking hole is offset from the at least one aft radiographic marking hole by a 45° angle.

8. A gas turbine engine compressor rotor assembly, comprising:
   a weldment member having
      a plurality of compressor disks, each compressor disk comprising a forward welding member having an annular shape with a forward welding face formed at one end of the annular shape, the forward welding face having at least one forward radiographic marking hole formed therein; and an aft welding member having an annular shape with an aft welding face formed at one end of the annular shape, the aft welding face having at least one aft radiographic marking hole formed therein, wherein the forward welding face of the forward welding member is aligned with the aft welding face of the aft welding member and the at least one forward radiographic marking hole is offset from the at least one aft radiographic marking hole angularly; and wherein each of the plurality of compressor disks including a plurality of rotor blade slots;

a plurality of compressor rotor blades, each located in one of the rotor blade slots.

9. A gas turbine engine compressor rotor assembly of claim 8, further comprising a plurality of forward radiographic marking holes equally spaced around a circumference of each forward welding member of each compressor disk; and a plurality of aft radiographic marking holes equally spaced around a circumference of each aft welding member of each compressor disk; and wherein each of the forward radiographic marking holes is offset angularly from each of the aft radiographic marking holes.

10. The gas turbine engine compressor rotor assembly of claim 8, wherein the at least one forward radiographic marking hole has a diameter less than or equal to 40 thousandths of an inch; and wherein the at least one aft radiographic marking hole has a diameter less than or equal to 40 thousandths of an inch.

11. The gas turbine engine compressor rotor assembly of claim 8, wherein the at least one forward radiographic marking hole has a hole depth greater than or equal to 50 thousandths of an inch and less than or equal to 70 thousandths of an inch; and wherein the at least one aft radiographic marking hole has a hole depth greater than or equal to 50 thousandths of an inch and less than or equal to 70 thousandths of an inch.

12. The gas turbine engine compressor rotor assembly of claim 8, wherein a radially inner edge of the at least one forward radiographic marking hole is disposed a distance from an outer edge of the forward welding member, the distance being equal to a weld penetration depth of the weldment member; and wherein a radially inner edge of the at least one aft radiographic marking hole is disposed a distance from an outer edge of the aft welding member, the distance being equal to a weld penetration depth of the weldment member.

13. The gas turbine engine compressor rotor assembly of claim 12, wherein the weld penetration depth of the weldment member is 75% of a thickness of the weldment member.

14. The gas turbine engine compressor rotor assembly of claim 8, wherein the at least one forward radiographic marking hole is offset from the at least one aft radiographic marking hole by a 45° angle.

15. A gas turbine engine including the compressor rotor assembly of claim 8.

* * * * *